United States Patent [19]

Davies

[11] Patent Number: 4,855,291
[45] Date of Patent: Aug. 8, 1989

[54] 1,4-DIHYDROQUINOLINES-3-CARBOXAMIDES

[75] Inventor: Roy V. Davies, Nottinghamshire, England

[73] Assignee: The Boots Company plc, England

[21] Appl. No.: 66,821

[22] Filed: Jun. 25, 1987

Related U.S. Application Data

[63] Continuation of Ser. No. 838,670, Mar. 12, 1986, abandoned, which is a continuation of Ser. No. 760,823, Jul. 31, 1985, abandoned.

[30] Foreign Application Priority Data

Aug. 15, 1984 [GB] United Kingdom ............... 84/20689
Feb. 13, 1985 [GB] United Kingdom ............... 85/03625

[51] Int. Cl.$^4$ ..................... A61K 31/47; C07D 215/56
[52] U.S. Cl. .................................. 514/312; 546/156; 546/153
[58] Field of Search ........................ 514/312; 546/156

[56] References Cited

U.S. PATENT DOCUMENTS

| | | | |
|---|---|---|---|
| 4,302,460 | 11/1981 | Davies et al. | 514/312 |
| 4,442,109 | 4/1984 | Davies | 546/153 |
| 4,450,167 | 5/1984 | LeMartret et al. | 514/312 |
| 4,596,807 | 6/1986 | Crosby | 514/474 |
| 4,610,991 | 9/1986 | Bailey | 514/318 |
| 4,659,718 | 4/1987 | Davies et al. | 546/153 |
| 4,671,959 | 6/1987 | Warren et al. | 514/464 |
| 4,772,614 | 9/1988 | Davies et al. | 546/156 |
| 4,786,644 | 11/1988 | Glamrowski et al. | 546/156 |

FOREIGN PATENT DOCUMENTS

| | | | |
|---|---|---|---|
| 70767 | 1/1983 | European Pat. Off. | 546/156 |
| 4412143 | 6/1969 | Japan . | |

OTHER PUBLICATIONS

Nakanishi et al., Derwent Abstract for Japanese Patent, (vol. 8), #44/12143, (6/2/69).
Kozello et al., Pharmaceutical Chemistry Journal, (Khimiko-Farmatsevticheski Zhurnal), vol. 5, pp. 21-22, (1971).
Erickson et al., J. of Med. Chem., vol. 22, pp. 816-823, (1979).
"Medicinal Chemistry", (2nd Ed.), Alfred Berger, Editor, Interscience Publishers (N.Y.), p. 43, (1960).
Abstract for EP 70767, (7/17/81).
Abstract for EP 40573, (11/25/81).
Abstract for JP 54/88276, (7/13/79).
Abstract for BE 814843, (11/12/74).
Abstract for FR 2193822, (3/29/74).
Abstract for DT 1908548, (11/5/70).
Abstract for FR 2532314, (3/2/84).
Abstract for JP 58/148817, (9/15/83).
Abstract for JP 58/148861, (9/5/83).
Abstract for BE 892148, (8/16/82).

Primary Examiner—Donald G. Daus
Assistant Examiner—E. Beinhardt
Attorney, Agent, or Firm—Jacobs & Jacobs

[57] ABSTRACT

Quinolones of the formula I

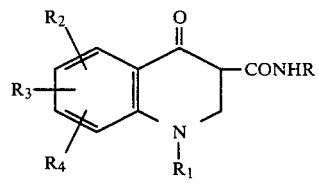

in which the dotted line between positions 2 and 3 of the quinolone ring represents an optional bond; R is hydrogen or lower alkyl; $R_1$ is lower alkyl; and $R_2$, $R_3$ and $R_4$, which may be the same or different, are hydrogen, halo, lower alkyl, lower alkoxy, lower alkylthio, lower alkylsulphinyl, lower alkylsulphonyl, trifluoromethyl, cyano, fluorinated lower alkoxy, phenyl optionally substituted by one or two substituents selected from lower alkyl, lower alkoxy, lower alkylthio, halo and trifluoromethyl, the group —OAr or the group —S(O)$_n$Ar in which Ar is phenyl optionally substituted by one or two substituents selected from lower alkyl, lower alkoxy, lower alkylthio, halo and trifluoromethyl and n is 0, 1 or 2, or the group —NR$_5$R$_6$ or the N-oxide thereof in which $R_5$ and $R_6$, which may be the same or different, are lower alkyl or, together with the nitrogen atom to which they are attached, form a 5-7 membered ring optionally containing an additional hetero atom selected from oxygen, nitrogen and sulphur have utility as antihypertensive agents.

Novel quinolones are those of the above-defined formula I, provided that (a) when the optional 2,3-bond is present $R_1$ is methyl and R is hydrogen, at least one of $R_2$, $R_3$ and $R_4$ is other than hydrogen and (b) when the optional 2,3-bond is present, R is lower alkyl and $R_3$ and $R_4$ are hydrogen, $R_2$ is other than hydrogen or lower alkoxy.

Pharmaceutical compositions comprising a novel quinolone of the above formula I together with a pharmaceutically acceptable carrier are described and claimed.

Processes for preparing the novel quinolones are also described.

6 Claims, No Drawings

1,4-DIHYDROQUINOLINES-3-CARBOXAMIDES

This is a continuation of Ser. No. 838,670, filed Mar. 12, 1986, now abandoned, which is a continuation of Ser. No. 760,823, filed July 31, 1985, now abandoned.

This invention relates to chemical compounds with therapeutic activity. More particularly, it relates to quinolones with antihypertensive activity, pharmaceutical compositions containing the quinolones and processes for preparing the quinolones.

In Japanese Patent Application No. 69 12143 (Chemical Abstracts Vol. 71, 1969, 101735q; Derwent Farmdoc Abstract 38127F) there are described quinolones of the formula A,

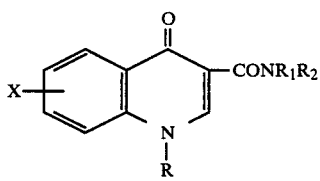

in which X is hydrogen or lower alkoxy, R is lower alkyl, phenyl or phenylalkyl, $R_1$ is hydrogen or lower alkyl, and $R_2$ is lower alkyl or $R_1$ and $R_2$, together with the nitrogen atom to which they are attached, form an alkyleneimino, morpholino or 4-lower alkylpiperazin-1-yl group. The compounds are stated to have antiinflammatory activity.

The present invention is based on our discovery

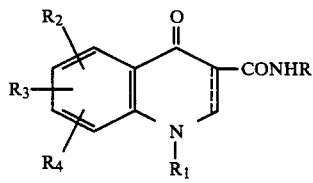

that quinolones of the formula I in which the dotted line between positions 2 and 3 of the quinolone ring represents an optional bond; R is hydrogen or lower alkyl; $R_1$ is lower alkyl; and $R_2$, $R_3$ and $R_4$, which may be the same or different, are hydrogen, halo, lower alkyl, lower alkoxy, lower alkylthio, lower alkylsulpinyl, lower alkylsulphonyl, triflourmethyl, cyano, fluorinated lower alkoxy, phenyl optionally substituted by one or two substituents selected from lower alkyl, lower alkoxy, lower alkylthio, halo and trifluoromethyl, the group —OAr or the group —S(O)$_n$Ar in which Ar is phenyl optionally substituted by one or two substituents selected from lower alkyl, lower alkoxy, lower alkylthio, halo and trifluoromethyl and n is 0, 1 or 2, or the group —NR$_5$R$_6$ or the N-oxide thereof in which $R_5$ and $R_6$, which may be the same or different, are lower alkyl or, together with the nitrogen atom to which they are attached, form a 5 to 7 membered ring optionally containing an additional hetero atom selected from oxygen, nitrogen and sulphur have antihypertensive activity. The compounds reduce blood pressure when administered to hypertensive mammals.

Accordingly the present invention provides a method for reducing blood pressure in a hypertensive mammal which comprises the administration of a compound of formula I as hereinbefore defined.

Many of the compounds of formula I are novel. The present invention provides novel quinolones of formula I provided that (a) when the optional 2,3-bond is present, $R_1$ is methyl and R is hydrogen, at least one of $R_2$, $R_3$ and $R_4$ is other than hydrogen and (b) when the optional 2,3-bond is present, R is lower alkyl and $R_3$ and $R_4$ are hydrogen, $R_2$ is other than hydrogen or lower alkoxy.

The term "lower" signifies a group containing 1-8 carbon atoms, especially 1-4 carbon atoms. The groups may have a straight or branched chain. Examples of such groups include methyl, ethyl, propyl, isopropyl, butyl, secondary butyl, tertiary butyl, methoxy, ethoxy, propoxy, isopropoxy, methylthio, ethylthio, propylthio, isopropylthio, methylsulphinyl, ethylsulphinyl, propylsulphinyl, isopropylsulphinyl, methylsulphonyl, ethylsulphonyl, propylsulphonyl and isopropylsulphonyl. The group $R_1$ is preferably methyl. The term "halo" includes chloro, fluoro and bromo.

The term "fluorinated lower alkoxy" signifies a lower alkoxy group containing one or more fluorine atoms, for example difluoromethoxy and 2,2,2-trifluoroethoxy. Examples of the group —NR$_5$R$_6$ include dimethylamino, diethylamino, dipropylamino, N-methyl-N-ethylamino, pyrrolidin-1-yl piperidino, perhydro-1H-azepin-1-yl, morpholino, thiomorpholino and 4-methylpiperazin-1-yl.

It will be appreciated by those skilled in the art that, when the optional 2,3-bond is absent, the compounds of formula I have a chiral centre and thus exist in two enantiomeric forms. The present invention includes both enantiomers and mixtures thereof.

The compounds of formula I may form acid addition salts with strong acids, for example hydrochloric acid. It will be appreciated tat such salts, provided they are pharmaceutically acceptable, may be used in therapy in place of the corresponding compounds of formula I.

The present invention provides pharmaceutical compositions which comprise a compound of formula I together with a pharmaceutically acceptable carrier.

As used hereinafter, the term "active compound" denotes a novel quinolone of general formula I as hereinbefore defined. In therapeutic use, the active compound may be administered orally, rectally, parenterally or topically, preferably orally. Thus the therapeutic compositions of the present invention may take the form of any of the known pharmaceutical compositions for oral, rectal, parenteral or topical administration. Pharmaceutically acceptable carriers suitable for use in such compositions are well known in the art of pharmacy. The compositions of theinvention suitably contain 0.1-90% by weight of active compound. The compositions of the invention are generally prepared in unit dosage form.

Compositions for oral administration are the preferred compositions of the invention and these are the known pharmaceutical forms for such administration, for example tablets, capsules, syrups and aqueous or oily suspensions. The excipients used in the preparation of these compositions are the excipients known in the pharmacist's art. Tablets may be prepared by mixing the active compound with an inert diluent such as calcium phosphate in the presence of disintegrating agents, for example maize starch, and lubricating agents, for example magnesium stearate, and tableting the mixture by known methods. Such tablets may, if desired, be provided with enteric coatings by known methods, for example by the use of cellulose acetate phthalate. Similarly capsules, for examples hard or soft gelatin capsules, containing the active compound with or without added excipients, may be prepared by conventional means and, if desired, provided with enteric coatings in a known manner. Enteric coated compositions of the invention may be advantageous, depending on the nature of the active compound. The tablets and capsules may conveniently each contain 1–500 mg of the active compound. Other compositions for oral administration include, for example, aqueous suspensions containing the active compound in an aqueous medium in the presence of a non-toxic suspending agent such as sodium carboxymethylcellulose, and oily suspensions containing a compound of the present invention in a suitable vegetable oil, for example arachis oil.

Compositions of the invention suitable for rectal administration are the known pharmaceutical forms for such administration, for example, suppositories with cocoa butter or polyethylene glycol bases.

Compositions of the invention suitable for parenteral administration are the known pharmaceutical forms for such administration, for example, sterile suspensions in aqueous and oily media or sterile solutions in a suitable solvent.

Compositions for topical administration may comprise a matrix in which the active compound is dispersed so that the compound is held in contact with the skin in order to administer the active compound transdermally. Alternatively the active compound may be dispersed in a cream or ointment base.

In some formulations it may be beneficial to use the compounds of the present invention in the form of particles of very small size, for example, as obtained by fluid energy milling.

In the compositions of the present invention the active compound may, if desired, by associated with other compatible pharmacologically active ingredients, for example a β-blocker such as propranolol, oxyprenolol or timolol, or a diuretic such as bendrofluazide.

The therapeutic activity of the compounds of general formula I has been demonstrated by means of tests on standard laboratory animals. Such tests include, for example, the oral administration of the compounds to a strain of spontaneously hypertensive rat and the intra-duodenal administration of compounds to a strain of normotensive rat. Thus the compounds of formula I are useful for reducing blood pressure in hypertensive mammals. A suitable dose for enteral administration to mammals, including man, is generally within the range 0.1–25 mg/kg/day, more usually 0.5–10 mg/kg/day, given in single or divided doses. For parenteral administration, a suitable dose is generally within the range 0.01–2.5 mg/kg/day, especially 0.05–1.0 mg/kg/day. Oral administration is preferred.

The compounds of formula I may be prepared by reacting ammonia or an amine $RNH_2$ with an acylating agent capable of providing an acyl group of the formula II

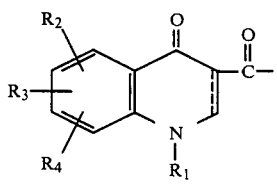

When the optional 2,3-bond is present, suitable acylating agents include the corresponding carboxylic acids, esters, for example a lower alkyl ester such as the methyl ester or ethyl ester, the acid anhydrides, mixed anhydrides with other acids such as ethoxyformic acid, an acid halide for example the acid chloride, and a mixture of the acid with a carboxiimide such as 1,3-dicyclohexylcarbodiimide. When the optional 2,3-bond is absent, suitable acylating agents include esters of the corresponding carboxylic acids, for example lower alkyl esters such as the methyl ester or ethyl ester. Depending upon the reaction cnditions, the ammonia or amine reactant may be, for example, gaseous ammonia or amine or a solution of ammonia or amine in a suitable solvent, for example water or an alcohol such as ethanol. It may be convenient to react the acid of formula III,

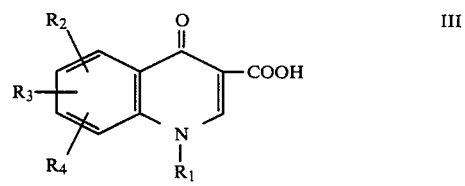

with a complex formed by reacting the amine $RNH_2$ with phosphorus trichloride. The reaction may be effected using methods analogous to those known in the art for preparing amides.

The acids of formula III in which the optional 2,3-bond is present, the corresponding lower alkyl esters and other acylating agents derived therefrom are compounds of known type and may be prepared by methods known in the art. For example, the lower alkyl esters in which $R_2$, $R_3$ and $R_4$ are other than the group $—NR_5R_6$ may be prepared by alkylation of a 4-hydroxyquinoline of the general formula IV,

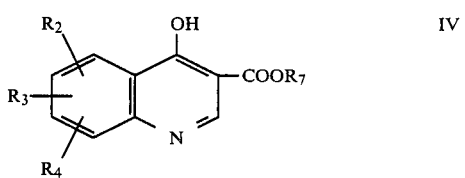

in which $R_7$ is lower alkyl, preferably methyl or ethyl.

Lower alkyl esters of carboxylic acids corresponding to the acyl group of formula II in which the optional 2,3-bond is absent may be prepared by reaction of the anion of formula V

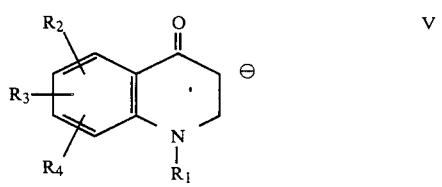

with a lower alkyl chloroformate, for example ethyl chloroformate.

The anion of formula V may be prepared by reacting the corresponding 2,3-dihydro-4-quinolinone with lithium diisoprpylamide or butyl lithium in a suitable solvent, for example tetrahydrofuran. The required 2,3- dihydro-4-quinolinones may be prepared by alkylation of the corresponding compounds with no substituent in the 1-position.

The lower alkyl esters of the acids of formula III may be converted to the corresponding carboxylic acids or other acylating agents by methods known in the art.

The compounds of formula I in which the 2,3-bond is present, $R_2$, $R_3$ and $R_4$ are other than cyano and R is hydrogen may also be prepared by hydration of a nitrile of formula VI

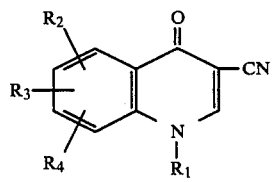

in which $R_2$, $R_3$ and $R_4$ are other than cyano.

The nitriles of formula VI in which $R_2$, $R_3$ and $R_4$ are other than the group $-NR_5R_6$ may be prepared by alkylation of a 4-hydroxyquinoline of formula VII

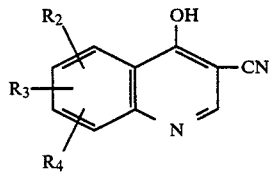

Compounds of formula VII are compounds of known type described, for example, in U.S. Pat. No. 4,035,368.

The compounds of formula I which contain a 7-substituent selected from cyano, lower alkoxy, lower alkylthio, lower alkylsulphonyl, fluorinated lower alkoxy, aryloxy, arylthio, arylsulphonyl and the amino group $-NR_5R_6$ may be prepared by reacting the corresponding 7-fluoro compounds with cyanide ion, lower alkoxide ion, lower alkanethiolate ion, lower alkanesulphonate ion, fluorinated lower alkoxide ion, aryloxide ion, arylthiolate ion, arylsulphonate ion, or the amine $HNR_5R_6$. Oxidation of the 7-amino group, for example with an organic percarboxylic acid, gives the N-oxide thereof.

The compounds of formula I which contain a 7-alkylsulphinyl, 7-arylsulphinyl, 7-alkylsulphonyl or 7-arylsulphonyl substituent may be prepared by oxidation of the corresponding 7-alkylthio or 7-arylthio compounds using, for example, an organic percarboxylic acid as the oxidising agent.

The compounds of formula I which contain a 7-(fluorinated lower alkoxy) substituent may also be prepared by reacting the corresponding 7-fluoro compound with hydroxide ion to give the corresponding 7-hydroxy compound, which is then reacted with the appropriate fluorinated chloroalkane, for example chlorodifluoromethane to give the 7-(fluorinated lower alkoxy) compound, for example the 7-difluoromethoxy compound.

The above-described reactions for preparing various 7-substituted compounds of formula I may be carried out using methods that are known in the art for analogous reactions. Thus, for example, in the reaction between a 7-fluoro compound of formula I and cyanide ion, the 7-fluoro compound and sodium cyanide may be heated in a suitable solvent, for example acetonitrile, preferably in the presence of a catalyst, for example a crown ether such as 18-crown-6.

Typical compounds of formula I include those identified in the Examples and the following compounds:

(A) 1-methyl-4-oxo-1,4-dihydroquinoline-3-carboxamide (B) 1,N-dimethyl-4-oxo-1,4-dihydroquinoline-3-carboxamide (C) 7-cyano-1-methyl-4-oxo-1,4-dihydroquinoline-3-carboxamide (D) 7-fluoro-6-methoxy-1-methyl-4-oxo-1,4-dihydroquinoline-3-carboxamide (E) 7-chloro-6-methoxy-1-methyl-4-oxo-1,4-dihydroquinoline-3-carboxamide (F) 6-methoxy-1,7-dimethyl-4-oxo-1,4-dihydroquinoline3-carboxamide (G) 1,7-dimethyl-4-oxo-1,4-dihydroquinoline-3-carboxamide As mentioned above, the therapeutic activity of the quinolones of general formula I has been demonstrated by tests which include (A) the oral administration of the compounds to a strain of spontaneously hypertensive rat and (B) the intraduodenal administration of the compounds to a strain of normotensive rat. These tests were carried out in the following way:

Test A

Female rats, weight range 180–240 g, of the Aoki-Okamoto strain of spontaneously hypertensive rat were used. The rats in groups of four were fasted overnight before administration of the test compound. Blood pressure was determined in the following way. The rats were placed in a cabinet kept at 38° C. with their tails protruding through holes in the cabinet. After 30 minutes in the cabinet blood pressure was measured using an inflatable cuff placed round the base of the tail and arterial pulsations monitored with a pneumatic pulse transducer. A pressure, greater than the expected blood pressure, was applied to the cuff, and this pressure was slowly reduced. The pressure in the cuff at which arterial pulsations reappeared was taken as the blood pressure. The rats were removed from the cabinet and each group orally dosed with a given dose of the test compound given as a solution or suspension in 0.25% aqueous carboxymethylcellulose. In addition to the pre-dosing reading, blood pressure was measured at 1.5 and 5.0 hours after dosing. A compound was designated as active if it gave a reduction of blood pressure of 20% or greater at either of these time intervals.

Test B

Male normotensive rats (Wistar strain) of weight range 210–240 g were used. The rats were anaesthetised and cannulae placed in a carotid artery and in the duodenum. Blood pressure was recorded electronically by means of a pressure transducer connected to the arterial cannula. The test compound was administered into the duodenum as a solution or suspension in 0.25% aqueous carboxymethylcellulose. Blood pressure was recorded before dosing and for 30 minutes afterwards. Results were obtained as the mean of determinations in three rats per dosage level. Compounds which caused an obvious drug-related fall in blood pressure of 14% or greater during the 30 minute post-dose period were designated as active.

The compounds of formula I identified in the following Examples were active in Test A at a dose of 90 mg/kg or less: Examples 1, 2, 4, 5, 6, 7, 8 and 9. The above-identified compounds A and B were also active in this test at a dose of 90 mg/kg or less.

The compound of formula I identified in Example 3 was not active in Test A at a dosage of 90 mg/kg but was active in Test B at a dose of 90 mg/kg.

Compounds which have activity in Test A at a dose of 90 mg/kg or less are preferred.

The compounds of formula I in which the optional 2,3-bond is present are preferred over those in which this bond is absent.

A preferred sub-group of compounds of the present invention is that of the novel compounds of formula I in which $R_4$ is hydrogen and $R_2$ and $R_3$, which may be the same or different, are hydrogen, halo, lower alkyl, lower alkoxy, trifluoromethyl, cyano or fluorinated lower alkoxy.

A more particular preferred sub-group of compounds of the present invention is that of the formula VIII,

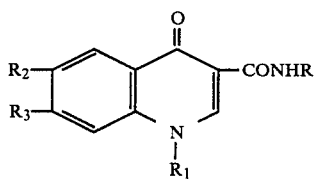

in which R is hydrogen or alkyl containing 1 to 4 carbon atoms, $R_1$ is alkyl containing 1 to 4 carbon atoms, $R_2$ is hydrogen, halo, alkyl containing 1 to 4 carbon atoms or alkoxy containing 1 to 4 carbon atoms and $R_3$ is hydrogen, halo, alkyl containing 1 to 4 carbon atoms, alkoxy containing 1 to 4 carbon atoms, trifluoromethyl, cyano or fluorinated alkoxy containing 1 to 4 carbon atoms, provided that (a) when R is hydrogen and $R_1$ is methyl, at least one of $R_2$ and $R_3$ is other than hydrogen, and (b) when R is alkyl containing 1-4 carbon atoms and one of $R_2$ and $R_3$ is hydrogen, the other of $R_2$ and $R_3$ is other than hydrogen or alkoxy containing 1-4 carbon atoms. A preferred value of $R_2$ is hydrogen. $R_1$ is preferably methyl.

The invention is illustrated by the following non-limitative Examples, in which parts and percentages are by weight and compositions of mixed solvents are given by volume. Novel compounds were characterised by one or more of the following spectroscopic techniques: nuclear magnetic resonance, infra red and mass spectroscopy. Temperatures are given in degrees Celsius. The term "IMS" signifies industrial methylated spirit.

EXAMPLE 1

(a) A mixture of ethyl 7-fluoro-4-hydroxyquinoline-3-carboxylate (4.7 g), anhydrous potassium carbonate (3.0 g), dimethyl sulphate (2.52 g) and butanone (200 ml) was boiled under reflux for 14 hours. The solvent was evaporated and the residue was triturated with dichloromethane (150 ml). The mixture was filtered and the filtrate was evaporated to a small volume. Diethyl ether was added, causing a solid to precipitate. The solid was collected, washed with ether, dried and recrystallised from IMS to give the novel compound ethyl 7-fluoro-1-methyl-4-oxo-1,4-dihydroquinoline-3-carboxylate, m.p. 164°–166°.

(b) A mixture of the above carboxylate ester (19.0 g), aqueous ammonia (specific gravity 0.88, 750 ml) and capryl alcohol (2 drops) was stirred on a steam bath for 1.5 hours, then cooled to room temperature. The solid product was collected by filtration and recrystallised from IMS/water 3:2 to give the novel compound 7-fluoro-1-methyl-4-oxo-1,4-dihydroquinoline3-carboxamide, m.p. 317°–318°.

EXAMPLE 2

A mixture of ethyl 6,7-dimethoxy-1-methyl-4-oxo-1,4-dihydroquinoline-3-carboxylate (4.0 g) and ethanol saturated with ammonia (200 ml) was heated at 100° in a stainless steel pressure vessel for 20 hours, then cooled to ambient temperature. The mixture was evaporated and the residue purified by high pressure liquid chromatography on silica using dichloromethane IMS 96.5:3.5 as the eluent. The resulting product was recrystallised from IMS to give the novel compound 6,7-dimethoxy-1-methyl-4-oxo-1,4-dihydroquinoline-3-carboxamide, m.p. 323°–325° (dec).

EXAMPLE 3

(a) A mixture of 3-methoxy-N-methylaniline (44 g) and diethyl ethoxymethylenemalonate (69 ml) was heated on a steam bath for 2 hours, the ethanol formed being removed by distillation. The residue was cooled to ambient temperature to give the novel compound diethyl (3-methoxy-N-methylanilino)methylenemalonate as an oil.

(b) A mixture of all the malonate ester produced in the above stage and polyphosphoric acid (250 ml) was heated on a steam bath for 40 minutes then cooled to room temperature. The mixture was poured into a mixture of ice and water and the resulting mixture neutralised with 5N aqueous sodium hydroxide. The resulting precipitate was collected by filtration, washed with water, dried and recrystallised from IMS to give the novel compound ethyl 7-methoxy-1-methyl-4-oxo-1,4-dihydroquinoline-3-carboxylate, m.p. 198°–200°.

(c) A mixture of the above carboxylate ester (11.8 g) and aqueous ammonia (specific gravity 0.88, 300 ml) was stirred and heated on a steam bath for 6 hours. The solid product was collected by filtration, dried and recrystallised from IMS to give the novel compound 7-methoxy-1-methyl-4-oxo-1,4-dihydroquinoline-3-carboxamide, m.p. 304°–306°.

EXAMPLE 4

A mixture of ethyl 7-chloro-1-methyl-4-oxo-1,4-dihydroquinoline-3-carboxylate (5.0 g) and aqueous ammonia (specific gravity 0.88, 100 ml) was stirred and heated on a steam bath for 3.5 hours. More aqueous ammonia (100 ml) was added and heating was continued for a further 21 hours. The mixture was cooled in ice. The solid product was collected by filtration and dried to give the novel compound 7-chloro-1-methyl-4-oxo-1,4-dihydroquinoline-3-carboxamide, m.p. >240°.

EXAMPLE 5

(a) Iodomethane (7.7 g) was added dropwise to a stirred mixture of ethyl 7-ethyl-4-hydroxyquinoline-3-carboxylate (12.1 g), anhydrous potassium carbonate (6.8 g) and dimethylformamide (125 ml) at ambient temperature. Stirring was continued for 30 hours. The solution was cooled in ice, diluted with 2 volumes of water and extracted with dichloromethane (3×100 ml). The extracts were combined, washed with water, dried over anhydrous sodium sulphate and evaporated. The residual oil was triturated with cold ethyl acetate. The resulting solid was collected, washed with ethyl acetate and recrystallised from ethyl acetate to give the novel compound ethyl 7-ethyl-1-methyl-4-oxo-1,4-dihydroquinoline-3-carboxylate, m.p. 92°–94°.

(b) A mixture of the above carboxylate ester (5.87 g) and aqueous ammonia (specific gravity 0.88, 100 ml) was stirred and heated on a steam bath for 4 hours. More aqueous ammonia (100 ml) was added and heating continued for 2 hours. More aqueous ammonia (100 ml) was added and heating was continued overnight. The mixture was then cooled to ambient temperature. The resulting precipitate was collected, washed with water and dried to give the novel compound 7-ethyl-1-methyl-4-oxo-1,4-dihydroquinoline-3-carboxamide, m.p. 255°–256°.

EXAMPLE 6

(a) A mixture of ethyl 4-hydroxy-7-trifluoromethylquinoline-3-carboxylate (370.5 g), anhydrous potassium carbonate (179.4 g), iodomethane (202.4 g) and anhydrous dimethylformamide (2 liters) was stirred at room temperature overnight. More dimethylformamide (500 ml) was added and stirring was continued for 24 hours. The dimethylformamide was distilled off in vacuo and water (2 litres) was added to the residue. The resulting solid was collected, washed with water, dried and recrystallised from IMS to give the novel compound ethyl 1-methyl-4-oxo-7-trifluoromethyl-1,4-dihydroquinoline-3-carboxylate, m.p. 222°–224°.

(b) A mixture of the above ester (6.8 g) and aqueous ammonia (specific gravity 0.88, 100 ml) was stirred and heated on a steam bath. More aqueous ammonia (100 ml) was added and heating and stirring was continued for 24 hours. The mixture was cooled to ambient temperature. The resulting solid was collected, washed with water and dried. The solid was recrystallised by dissolving it in boiling dichloromethane/IMS 1:1, removing the dichloromethane by azeotropic distillation, and cooling the mixture. The resutling solid was collected and dried to give the novel compound 1-methyl-4-oxo-7-trifluoromethyl-1,4-dihydroquinoline-3-carboxamide, m.p. 288°–292°.

EXAMPLE 7

Boron trifluoride etherate (5 ml) was added cautiously to a mixture of ethyl 7-chloro-1-methyl-4-oxo-1,4-dihydroquinoline-3-carboxylate (5 g) and a solution of methylamine in IMS (32%; 35 ml) and the mixture was boiled under reflux for 8 hours. The same quantities of boron trifluoride etherate and methylamine in IMS were added and the mixture was boiled under reflux for 24 hours. The same quantities of boron trifluoride etherate and methylamine in IMS were added and the mixture was boiled under reflux for 8 hours. The mixture was kept at ambient temperature for 16 hours and then filtered. The residue was washed with IMS, dried and recrystallised from aqueous IMS to give the novel compound 7-chloro-1,N-dimethyl-4-oxo-1,4-dihydroquinoline-3-carboxamide, m.p. 260°–263°.

EXAMPLE 8

(a) In a similar manner to that described in Example 5(a), ethyl 7-tert-butyl-4-hydroxyquinoline-3-carboxylate was methylated to give the novel compound ethyl 7-tert-butyl-1-methyl-4-oxo-1,4-dihydroquinoline-3-carboxylate, m.p. 137.5°–139.5°.

(b) A mixture of the above ester (7.66 g) and methanol saturated with ammonia (150 ml) was heated in a stainless steel pressure vessel at 150° for 23 hours. After cooling, the solid product was collected by filtration and washed with methanol. The product was purified by flash chromatography [described in J. Org. Chem., Vol. 43, 2923–5 (1978)] over a silica gel sold under the trade name Kieselgel 60 using dichloromethane:IMS 95:5 as the eluent. There was obtained the novel compound 7-tert-butyl-1-methyl-4-oxo-1,4-dihydroquinoline-3-carboxamide, m.p. 268°–270°. (from IMS).

EXAMPLE 9

(a) In a similar manner to that described in Example 1(a), ethyl 6-fluoro-4-hydroxyquinoline-3-carboxylate was methylated to give the novel compound ethyl 6-fluoro-1-methyl-4-oxo-1,4-dihydroquinoline-3-carboxylate, m.p. 193°–195°.

(b) A mixture of the above ester (10 g), aqueous ammonia solution (specific gravity 0.88, 200 ml) and capryl alcohol (a few drops) was stirred and heated at 95°–100° for 24 hours. More ammonia solution (150 ml) was added and stirring at 95°–100° was continued for 24 hours. The mixture was cooled to ambient temperature. The solid product was collected by filtration and washed with boiling IMS to give the novel compound 6-fluoro-1-methyl-4-oxo-1,4-dihydroquinoline-3-carboxamide, m.p. 295°–299°.

EXAMPLE 10

In the preparation of capsules, 100 parts by weight of active compound and 250 parts by weight of lactose are de-aggregated and blended. The mixture is filled into hard gelatin capsules, each capsule containing 100 mg of active compound.

EXAMPLE 11

Tablets are prepared from the following ingredients.

|  | parts by weight |
|---|---|
| Active compound | 100 |
| Lactose | 100 |
| Maize starch | 22 |
| Polyvinylpyrrolidone | 10 |
| Magnesium stearate | 3 |

The active compound, the lactose and some of the starch are de-aggregated, blended and the resulting mixture is granualted with a solution of the polyvinylpyrrolidone in ethanol. The dry granulate is blended with the magnesium stearate and the rest of the starch. The mixture is then compressed in a tableting machine to give tablets containing 100 mg active compound.

EXAMPLE 12

Tablets are prepared by the method of Example 11. The tablets are enteric coated in a conventional manner using a solution of 20% cellulose acetate phthalate and 3% diethyl phthalate in ethanol:dichloromethane 1:1.

EXAMPLE 13

In the preparation of suppositories, 100 parts by weight of active compound is incorporated in 1300 parts by weight of tri-glyceride suppository base and the mixture formed into suppositories each containing 100 mg of active compound.

I claim:

1. A compound selected from the group consisting of
   (a) 7-fluoro-1-methyl-4-oxo-1,4-dihydroquinoline-3-carboxamide;

(b) 7-chloro-1-methyl-4-oxo-1,4-dihydroquinoline-3-carboxamide;

(c) 1-methyl-4-oxo-7-trifluoromethyl-1,4,-dihydroquinoline-3-carboxamide;
and (d) 7-chloro-1,N-dimethyl-4-oxo-1,4-dihydroquinoline-3-carboxamide.

2. The compound according to claim 1 whichis 7-chloro-1,N-dimethyl-4-oxo-1,4-dihydroquinoline-3-carboxamide.

3. A pharmaceutical composition useful for reducing blood pressure in humans and animals which comprises a therapeutically effective amount of a compound selected from the group consisting of (a) 7-fluoro-1-methyl-4-oxo-1,4-dihydroquinoline-3-carboxamide;

(b) 7-chloro-1-methyl-4-oxo-1,4-dihydroquinoline-3-carboxamide;

(c) 1-methyl-4-oxo-7-trifluoromethyl-1,4-dihydroquinoline-3-carboxamide;
and (d) 7-chloro-1,N-dimethyl-4-oxo-1,4-dihydroquinoline-3-carboxamide, in combination with a pharmaceutically acceptable carrier.

4. A composition according to claim 3 in which the compound is 7-chloro-1,N-dimethyl-4-oxo-1,4,-dihydroquinoline-3-carboxamide.

5. A method of reducing blood pressure in a hypertensive human or animal which comprises administering to such a human or animal in need thereof a therapeutically effective amount of a compound selected from the group consisting of (a) 7-fluoro-1-methyl-4-oxo-1,4-dihydroquinoline-3-carboxamide;

(b) 7-chloro-1-methyl-4-oxo-1,4-dihydroquinoline-3-carboxamide;

(c) 1-methyl-4-oxo-7-trifluoromethyl-1,4-dihydroquinoline-3-carboxamide;
and (d) 7-chloro-1,N-dimethyl-4-oxo-1,4-dihydroquinoline-3-carboxamide, in combination with a pharmaceutically acceptable carrier.

6. A method according to claim 5 in which the compound is 7-chloro-1,N-dimethyl-4-oxo-1,4-dihydroquinoline-3-carboxamide.

* * * * *

UNITED STATES PATENT AND TRADEMARK OFFICE
CERTIFICATE OF CORRECTION

PATENT NO. : 4,855,291

DATED : August 8, 1989

INVENTOR(S) : Roy V. Davies

It is certified that error appears in the above-identified patent and that said Letters Patent is hereby corrected as shown below:

In the title, "1,4-Dihydroquinolines-3-Carboxamides" should read "1,4-Dihydroquinoline-3-Carboxamides".

In the Abstract, the formula I should contain a dotted line between positions 2 and 3 of the quinolone ring representing an optional double bond.

In Column 1, line 49, "trifluormethyl" should read "trifluoromethyl".

In Column 2, line 35, "tat" should read "that".

In Column 2, line 51, a space should be inserted between the words "the" and "invention".

In Column 4, line 7 "carboxiimide" should read "carbodiimide".

In Column 4, line 12, "cnditions" should read "conditions".

In Column 4, line 67 "diisoprpylamide" should read "diisopropylamide".

In Column 6, line 16, a hyphen should be inserted between "quinoline" and "3".

In Column 8, line 12 a "/" should be inserted between "dichloromethane" and "IMS".

UNITED STATES PATENT AND TRADEMARK OFFICE
CERTIFICATE OF CORRECTION

PATENT NO. : 4,855,291

DATED : August 8, 1989

INVENTOR(S) : Roy V. Davies

It is certified that error appears in the above-identified patent and that said Letters Patent is hereby corrected as shown below:

In Column 9, line 37, "resutling" should read "resulting".

Signed and Sealed this

Twenty-first Day of August, 1990

*Attest:*

HARRY F. MANBECK, JR.

*Attesting Officer*     *Commissioner of Patents and Trademarks*